United States Patent
Mack

Patent Number: 5,994,712
Date of Patent: Nov. 30, 1999

[54] BELT FLAW DETECTOR

[76] Inventor: John Edward Mack, 417 Parkway Blvd., Elizabethton, Tenn. 37643

[21] Appl. No.: 08/902,534

[22] Filed: Jul. 29, 1997

[51] Int. Cl.[6] .................................................. G01N 21/86
[52] U.S. Cl. ................................ 250/559.45; 250/559.42
[58] Field of Search ......................... 250/559.45, 559.43, 250/559.42, 223 B, 223 R

[56] References Cited

U.S. PATENT DOCUMENTS

| | | | |
|---|---|---|---|
| 3,700,909 | 10/1972 | Murray et al. | 250/559.42 |
| 3,741,663 | 6/1973 | Nevins | 250/559.42 |
| 4,306,813 | 12/1981 | Sick | 356/431 |
| 4,591,726 | 5/1986 | Schenk | 250/559.03 |
| 4,788,442 | 11/1988 | Sabater | 250/559.36 |
| 4,842,413 | 6/1989 | Kuijpers | 356/426 |
| 4,866,289 | 9/1989 | Kawamura | 250/559.22 |
| 4,933,566 | 6/1990 | Sagaguchi | 250/559.36 |
| 4,988,204 | 1/1991 | Sagaguchi | 356/430 |
| 5,095,214 | 3/1992 | Eder | 250/559.03 |

*Primary Examiner*—Que T. Le
*Attorney, Agent, or Firm*—Adrian J Good

[57] ABSTRACT

A belt flaw detector has a light source, a sensor, and processing and signalling means to indicate and warn of the flaw in the belt.

10 Claims, 1 Drawing Sheet

BELT FLAW DETECTOR

BACKGROUND OF THE INVENTION

In many present day automobiles, a timing belt has the vital functions of operating the camshaft controlling the intake and exhaust valves in synchronicity with the ignition and fuel injection systems. The advancements in design and materials for the modern car have brought better performance, lower fuel consumption, and lessened air pollution, all of which come at a price of necessarily improved reliability and precision of all components.

One of the components of the modern engine, the timing belt, which operates the camshaft and ignition components, is a most critical and yet one of the most vulnerable components, since it is composed of fiber reinforced high polymer elastomer, an organic structure in a high temperature stressful environment. A failure of the timing belt can be catastrophic, destroying the whole engine, and to the end of preventing or delaying this failure, much research and development has gone into providing a durable combination of reinforcing fiber and elastomer.

In spite of these efforts, timing belts still fail, usually at the most inopportune times and places in which the engine has been overstressed e.g. in a desert with its high temperature.

1. U.S. Pat. No. 5,095,214 discloses a hole seeking device for a web using two laser scanning devices and an electronic processor comparing the signals thus detected.

2. U.S. Pat. No. 4,988,204 discloses a light scanning device for detecting a flaw in the joint between the leader and tape in audio and video cassettes.

3. U.S. Pat. No. 4,933,566 discloses a light scanning device for detecting edge flaws using the differential between satisfactory and unsatisfactory edges of a magnetic tape.

4. U.S. Pat. No. 4,866,289 discloses a flaw detector for wound yarn packages having two light sources and sensors and a comparator for determining if the yarn package is faulty.

5. U.S. Pat. No. 4,842,413 discloses a laser apparatus useful for inspecting welds in belt layers on radial tires.

6. U.S. Pat. No. 4,788,442 discloses a laser inspection device for detecting flaws on the edges of a moving sheet of paper or cardboard, using light transmission as the flaw detecting means.

7. U.S. Pat. No. 4,591,726 discloses an optical laser scanning device for detecting a flaw in a web of rapidly advancing material.

8. U.S. Pat. No. 4,306,813 discloses an optical scanner for detecting color and surface distortion in a strip of material.

SUMMARY OF THE INVENTION

A timing belt is continually sensed while in operation in an automobile engine by an electro-optic light source and sensor, providing a signal to an electronic computer module and an indicator or automatic safety actuator.

DESCRIPTION OF THE INVENTION

Figure 1:
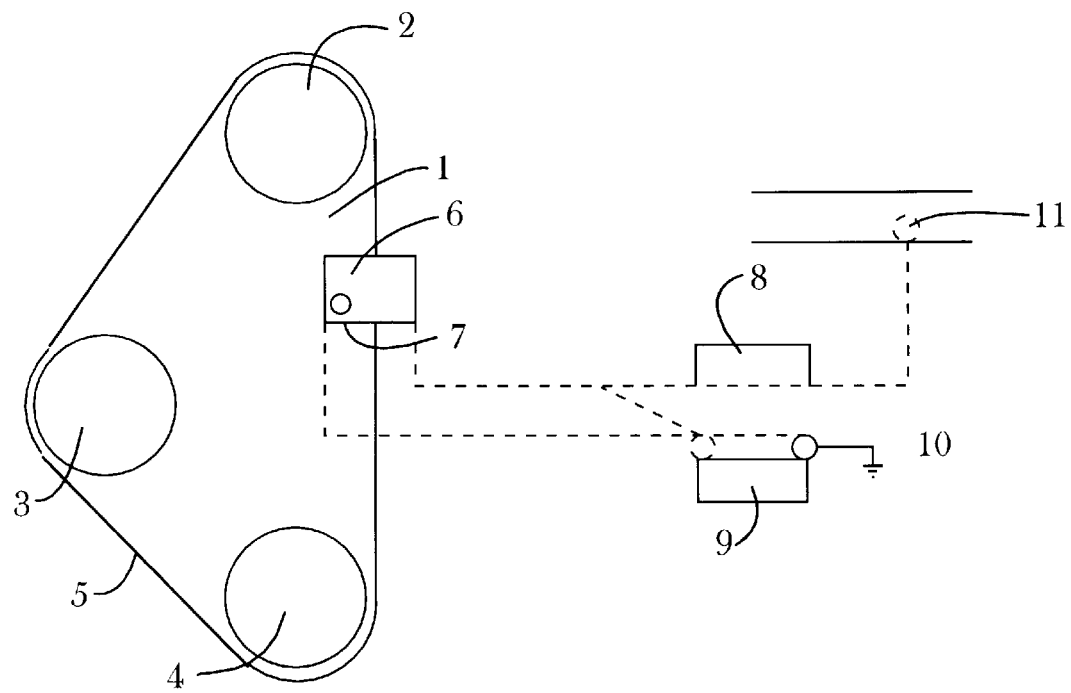
In FIG. 1 the engine block 1, not actually shown, is the base for cam 2, water pump 3, and crank 4, with timing belt 5 operating cam 2 and water pump 3 from crank 4. A light source 6 directs a beam of light 12 on belt 5. Any break in belt 5 will allow light 12 to reach sensor 7, which will then send a signal to electronic computer module 8 for processing and possible amplification, actuating indicator 11. The light source, sensor, module and indicator are all powered by the electrical system exemplified by battery 9, grounded at 10. Although the drawing displays the light source 6 on the interior of the belt, it can also be reversed, with the light on the exterior.
Figure 2:
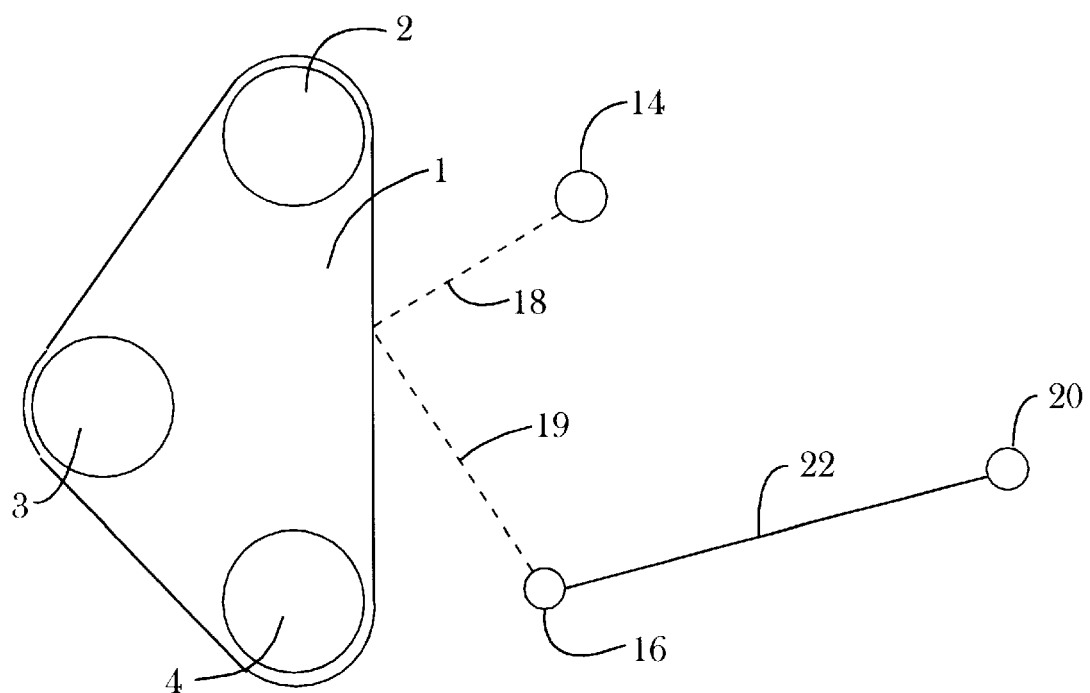
FIG. 2 shows the belt 5 as in FIG. 1, with light source 14, light beam 18, impinging on belt 5, reflecting to sensor 16 through reflected beam 19, with connection 22, to computerized control 20. While this invention is shown as applied to an internal combustion automobile engine it could be applied to any engine relying on a belt or to any belt-driven apparatus. The electronic computer module must be able to differentiate the signal from an extraneous source or background coming from the sensor 7, which would normally be a photocell, charge coupled semiconductor, or other light-sensitive device, from a signal indicating a flaw of significant magnitude in the belt. The light sensor may alternately be connected to processing means by a fiber optic cable, with light processing and conversion to an electrical signal to the indicator or actuator. The indicator 11 can be a warning device such as a lamp, horn, or an automatic actuator which could stop the engine or apparatus, normally by switching the ignition and fuel pump off. While the light source normally will be a source of visible light, any other source and sensor combination may be used, such as an infrared or ultraviolet combination. No limitation is put on these combinations.

In a preferred embodiment of my invention, on an automobile engine a narrow LED beam, laser or other suitable light source is directed at one side of an internal combustion engine timing belt. A photocell on the other side of the belt is situated such that when a flaw or break in the belt occurs, the beam of light will impinge on the photocell, which will then generate a current, sending it to an electronic module which will process it, compare it to background signal noise and amplify it, if necessary sending a signal to an LED (light emitting diode) or other indicator on the dash of the car. The driver is then warned to replace the belt before it fails catastrophically and damages the engine. Alternately the signal may trigger an automatic ignition cutoff to prevent further damage to the engine.

The timing belt must be resistant to heat under the hood of the vehicle and exposure to oil. A common material used in timing belts is a chloroprene—highly saturated nitrile rubber or totally highly saturated nitrile rubber, with heat resistant synthetic fiber reinforcement.

It is also feasible to have the light source and the photo sensor on the same side of the belt, the light source impinging on the belt at an angle, and the sensor at an equal and opposite angle to receive a reflected light beam, thus disclosing a possible flaw prior to an actual discontinuity in the belt.

The signal processor is preferably a transistor chip capable of differentiating a default or flaw signal from the background radiation, amplifying the signal and transmitting it to a warning signal or to an automatic cutoff switch killing the ignition to prevent further damage to the engine.

I claim:

1. A belt flaw detector for a vehicle timing belt comprising a light source impinging at one side on a flexible belt, a light sensor situated on the opposite side of said belt at a position whereby a flaw or discontinuity in said belt allows the beam of the light from said source to reach and impinge on said sensor, whereby said sensor is activated to transform the beam of light to an electrical signal and thus sending a signal indicating a flaw to processing and warning or actuating means to stop the movement of the belt.

2. The belt flaw detector of claim 1 wherein said belt is a component of an internal combustion engine.

3. The belt flaw detector of claim 2 wherein said belt is a timing belt.

4. The belt flaw detector of claim 2 wherein said belt is a component of an auto or truck engine.

5. The belt flaw detector of claim 1 wherein the light source is selected from a group consisting of lasers, light-emitting diodes, or other device emitting light in the visible ultra-violet, or infra-red spectra.

6. The belt flaw detector of claim 1 wherein the sensor comprises a photocell capable of providing an electrical signal to processing means.

7. The belt flaw detector of claim 1 wherein the processing means are capable of receiving an electrical signal from the light sensor, differentiating signal indicating a flaw from a signal indicating no flaw, processing said differentiated flaw signal and sending the resulting flaw signal to warning or actuating means.

8. A belt flaw indicator for a vehicle timing belt comprising a light source impinging a beam of light at an angle other than at 90° to the plane and on one side of the belt, a sensor capable of receiving said beam of light from said light source, said sensor placed equal and opposite angle from 90° on the other side of said belt whereby said beam of light will impinge on said sensor to indicate a flaw when said belt has a flaw, the capable of converting the signal from the beam of light to an electrical signal and capable of sending said signal to processing means capable of giving a warning signal or activating automatic shutoff means to stop the movement of the belt.

9. A belt flaw detector for a vehicle combustion engine timing belt comprising a light source projecting a light beam on on one side of said belt, a photo sensor situated on the opposite side of said belt at an equal angle from said light source capable to receive a signal from said beam indicating a discontinuity in said belt, said sensor capable of converting said light beam signal to an electrical signal, transmission means to carry said electrical signal to processing means, said processing means capable of sending a warning signal to warning display means in said vehicle or alternately to actuate a cutoff switch to the ignition of said vehicle to stop the engine and prevent damage to the engine.

10. A belt flaw detector for an internal combustion engine comprising a light source at an angle other than at 90° to said belt, a sensor on the same side of said belt at an equal and opposite angle to said belt situated to receive a reflected beam from said light source whereby a flaw or discontinuity in said belt will interrupt said reflected beam, said sensor capable converting said beam to an electrical signal and sending a signal to processing means capable of differentiating a normal uninterrupted signal from an interrupted default signal, processing said signal and sending an electrical signal to warning indicator means or to automatic actuator means cutting off the ignition of the combustion engine.

* * * * *